United States Patent
Antunes et al.

(10) Patent No.: US 12,048,537 B2
(45) Date of Patent: Jul. 30, 2024

(54) MITIGATING INPUT BLOOD PRESSURE VARIABILITY IN AUTOREGULATION MONITORING

(71) Applicant: Covidien LP, Mansfield, MA (US)

(72) Inventors: Andre Antunes, Edinburgh (GB); Paul S. Addison, Edinburgh (GB); Dean Montgomery, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 1001 days.

(21) Appl. No.: 16/154,288

(22) Filed: Oct. 8, 2018

(65) Prior Publication Data

US 2020/0107763 A1  Apr. 9, 2020

(51) Int. Cl.
| | |
|---|---|
| A61B 5/1455 | (2006.01) |
| A61B 5/0225 | (2006.01) |
| A61B 5/03 | (2006.01) |
| A61B 5/00 | (2006.01) |
| A61B 5/026 | (2006.01) |
| A61B 5/0295 | (2006.01) |

(52) U.S. Cl.
CPC ........ *A61B 5/14553* (2013.01); *A61B 5/0225* (2013.01); *A61B 5/031* (2013.01); *A61B 5/0261* (2013.01); *A61B 5/0295* (2013.01); *A61B 5/4064* (2013.01); *A61B 5/7246* (2013.01)

(58) Field of Classification Search
None
See application file for complete search history.

(56) References Cited

U.S. PATENT DOCUMENTS

| | | |
|---|---|---|
| 6,599,251 B2 | 7/2003 | Chen et al. |
| 7,182,602 B2 | 2/2007 | Lakin et al. |
| 7,597,666 B2 | 10/2009 | Frinak et al. |
| 8,062,224 B2 | 11/2011 | Ragauskas et al. |
| 8,366,627 B2 | 2/2013 | Kashif et al. |
| 8,821,408 B2 | 9/2014 | Hu et al. |
| 9,414,755 B2 | 8/2016 | Lowe |

(Continued)

OTHER PUBLICATIONS

Kawarada, A., et al. "Ambulatory monitoring of indirect beat-to-beat arterial pressure in human fingers by a volume-compensation method." Medical and Biological Engineering and Computing 29 (1991): 55-62. (Year: 1991).*

(Continued)

*Primary Examiner* — Jacqueline Cheng
*Assistant Examiner* — Jairo H Portillo
(74) *Attorney, Agent, or Firm* — Fletcher Yoder, P.C.

(57) ABSTRACT

A system for monitoring autoregulation may include processing circuitry configured to receive a blood pressure signal indicative of an acquisition blood pressure of a patient at an acquisition site and an oxygen saturation signal indicative of an oxygen saturation of the patient. The processing circuitry may determine an altered blood pressure value indicative of a reference blood pressure of the patient at a reference site based on the blood pressure signal. The altered blood pressure value may enable a more accurate subsequent determination of a value indicative of the autoregulation status of the patient compared to an unaltered blood pressure value. In some examples, the processing circuitry may provide a signal indicative of the autoregulation status of the patient to an output device to enable a clinician to monitor the autoregulation status of the patient.

35 Claims, 6 Drawing Sheets

(56) References Cited

U.S. PATENT DOCUMENTS

| | | |
|---|---|---|
| 9,861,317 B2 | 1/2018 | Ochs |
| 2009/0326386 A1 | 12/2009 | Sethi et al. |
| 2012/0215081 A1* | 8/2012 | Euliano .................. A61B 5/037 600/323 |
| 2013/0190632 A1 | 7/2013 | Baruch et al. |
| 2014/0073888 A1* | 3/2014 | Sethi .................. A61B 5/14551 600/324 |
| 2015/0133798 A1* | 5/2015 | Hu ...................... A61B 5/7225 703/2 |
| 2015/0230774 A1* | 8/2015 | Thai ...................... A61B 5/022 600/454 |
| 2016/0106372 A1* | 4/2016 | Addison .............. A61B 5/7246 600/324 |
| 2016/0113589 A1* | 4/2016 | Yoon .................. A61B 5/02108 600/485 |
| 2016/0324425 A1 | 11/2016 | Addison et al. |
| 2016/0367197 A1 | 12/2016 | Addison et al. |
| 2017/0000395 A1* | 1/2017 | Addison ................ G16H 50/20 |
| 2017/0095161 A1 | 4/2017 | Addison et al. |
| 2017/0105631 A1 | 4/2017 | Addison et al. |
| 2017/0105672 A1 | 4/2017 | Addison et al. |
| 2018/0014791 A1 | 1/2018 | Montgomery et al. |
| 2018/0049649 A1 | 2/2018 | Addison et al. |
| 2018/0110473 A1 | 4/2018 | Kim |

OTHER PUBLICATIONS

Chauhan S. et al.; "Femoral artery pressures are more reliable than radial artery pressures on initiation of cardiopulmonary bypass."; Journal of cardiothoracic and vascular anesthesia; Jun. 30, 2000; vol. 14, No. 3; pp. 274-6.

Czosnyka, M. et al.; "An Assessment of Dynamic Autoregulation from Spontaneous Fluctuations of Cerebral Blood Flow Velocity: A Comparison of Two Models, Index of Autoregulation and Mean Flow Index"; Anesthesia & Analgesia; Jan. 2008; vol. 106, Issue 1; pp. 234-239.

Steinmeier, R. et al.; "Continuous Cerebral Autoregulation Monitoring by Cross-Correlation Analysis"; Journal of Neurotrauma; Oct. 2002; vol. 19, Issue 10; pp. 1127-38.

U.S. Appl. No. 15/962,438, filed Apr. 25, 2018, naming inventors Addison et al.

\* cited by examiner

MITIGATING INPUT BLOOD PRESSURE VARIABILITY IN AUTOREGULATION MONITORING

TECHNICAL FIELD

This disclosure related to monitoring autoregulation status of a patient.

BACKGROUND

Clinicians may monitor one or more physiological parameters of a patient, e.g., to monitor a patient's cerebral autoregulation status. Cerebral autoregulation is the response mechanism by which an organism regulates cerebral blood flow over a wide range of systemic blood pressure changes through complex myogenic, neurogenic, and metabolic mechanisms. During autoregulation, cerebral arterioles dilate or constrict in an attempt to maintain appropriate blood flow. For example, as cerebral pressure decreases, cerebral arterioles dilate in an attempt to maintain blood flow. As cerebral pressure increases, cerebral arterioles constrict to reduce the blood flow that could cause injury to the brain.

SUMMARY

The present disclosure describes example devices, systems, and techniques for determining an altered blood pressure value indicative of a reference blood pressure of the patient at a reference site based on an acquisition blood pressure signal acquired at a different site, referred to herein as an acquisition site. For example, a system may be configured to alter an acquisition blood pressure signal acquired by a non-invasive blood pressure measurement at a peripheral site to represent blood pressure in the brain of the patient, such as the middle cerebral artery. In some examples, a system may determine an autoregulation status of a patient based on the altered blood pressure value and an oxygen saturation signal indicative of an oxygen saturation of the patient.

In some examples, a method includes receiving, by processing circuitry, a blood pressure signal indicative of an acquisition blood pressure of a patient at an acquisition site and an oxygen saturation signal indicative of an oxygen saturation of the patient. The method also includes determining, by the processing circuitry, an altered blood pressure value indicative of a reference blood pressure of the patient at a reference site based on the blood pressure signal, and determining, by the processing circuitry, a value indicative of the autoregulation status of the patient based on the altered blood pressure value and the oxygen saturation signal. The method also includes providing, by the processing circuitry, a signal indicative of the autoregulation status of the patient to an output device.

In some examples, a system includes a blood pressure sensor configured to generate a blood pressure signal indicative of an acquisition blood pressure of a patient at an acquisition site, an oxygen saturation sensor configured to generate an oxygen saturation signal indicative of an oxygen saturation of the patient, and processing circuitry. The processing circuitry is configured to receive the blood pressure signal from the blood pressure sensor and receive the oxygen saturation signal from the oxygen saturation sensor, determine an altered blood pressure value indicative of a reference blood pressure of the patient at a reference site based on the blood pressure signal, determine a value indicative of the autoregulation status of the patient based on the altered blood pressure value and the oxygen saturation signal, and provide a signal indicative of the autoregulation status of the patient to an output device.

In some examples, a non-transitory computer readable storable medium includes instructions that, when executed by processing circuitry, causes the processing circuitry to receive a blood pressure signal indicative of a blood pressure of a patient at an acquisition site and an oxygen saturation signal indicative of an oxygen saturation of the patient. The instructions, when executed by the processing circuitry, also cause the processing circuitry to determine an altered blood pressure value indicative of a reference blood pressure of the patient at a reference site based on the blood pressure signal, determine a value indicative of the autoregulation status of the patient based on the altered blood pressure value and the oxygen saturation signal, and provide a signal indicative of the autoregulation status of the patient to an output device.

The details of one or more examples are set forth in the accompanying drawings and the description below. Other features, objects, and advantages will be apparent from the description and drawings, and from the claims.

DETAILED DESCRIPTION

Figure 1:
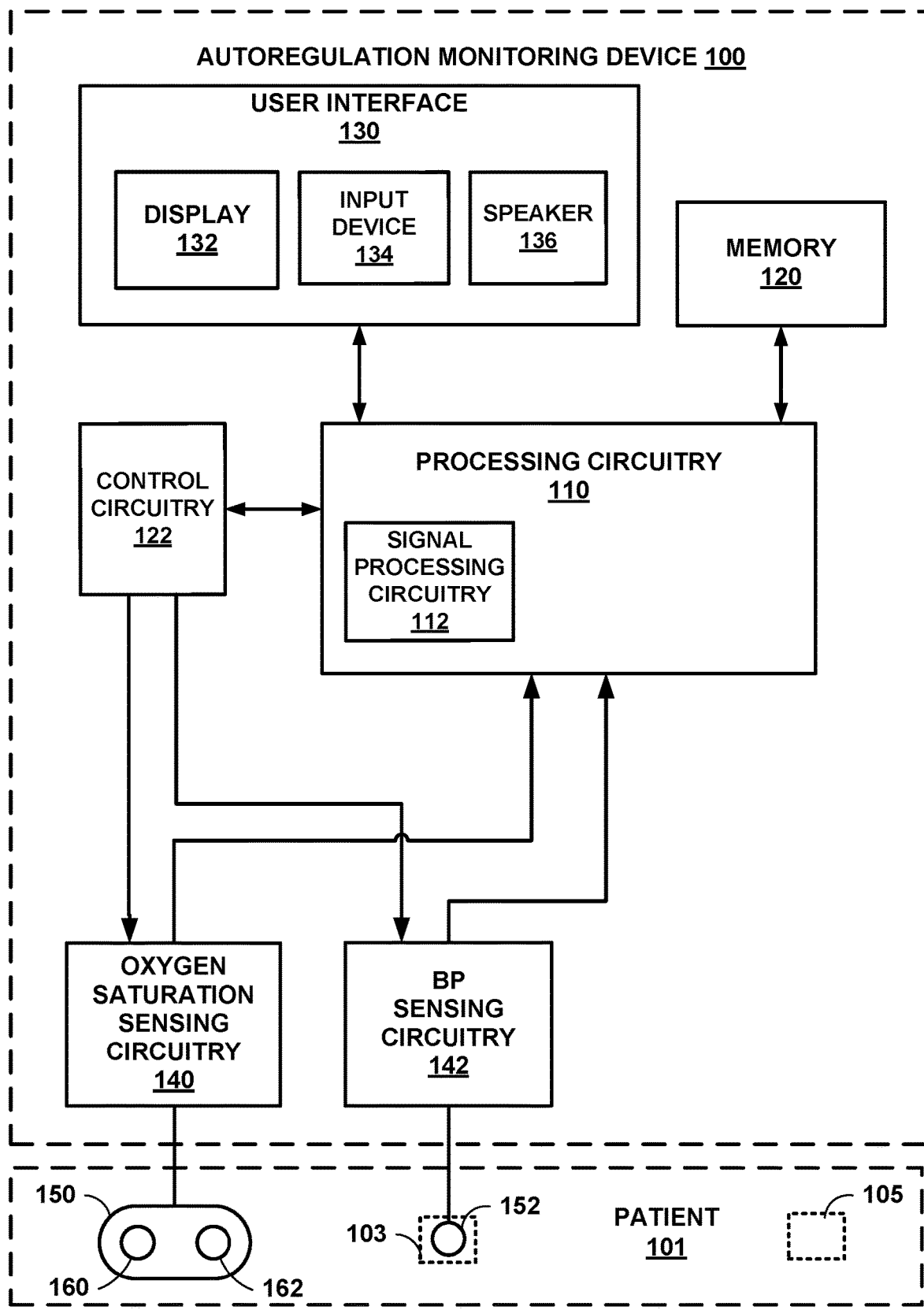
FIG. 1 is a conceptual block diagram illustrating an example system configured to monitor an autoregulation status of a patient.

An intact autoregulation status of a subject occurs over a range of blood pressures defined between a lower limit of autoregulation ("LLA") and an upper limit of autoregulation ("ULA"). An impaired autoregulation status occurs outside of the range of blood pressures defined between the LLA and the ULA and may occur when a patient's autoregulation process is not functioning properly. When a patient exhibits an impaired autoregulation status, the patient may experience inappropriate cerebral blood flow, which may be undesirable. For example, a drop in cerebral blood flow may cause ischemia, which may adversely affect brain cells. An increase in cerebral blood flow may cause hyperemia, which may result in swelling of the brain or edema. A clinician may monitor the autoregulation status of a patient, e.g., during a medical procedure, and take one or more actions to keep the patient in or bring the patient to an intact autoregulation status, such as by increasing or decreasing the patient's blood pressure.

A device configured to monitor an autoregulation status of a patient may be configured to determine the autoregulation status based on various physiological parameters of the patient, such as a blood pressure signal indicative of a blood pressure of a patient and an oxygen saturation signal indicative of blood oxygen saturation (e.g., regional oxygen saturation) of a patient. The present disclosure describes devices, systems, and techniques for determining blood pressure of a patient that can be used by a device to determine the autoregulation status of the patient.

In examples described herein, devices, systems, and techniques are configured to determine an altered blood pressure value indicative of a reference blood pressure of a patient at a reference site based on an acquisition blood pressure signal acquired at an acquisition site, which is different from the reference site. For example, the reference site may be more difficult to reach with a blood pressure sensor compared to the acquired site, e.g., may require more invasive pathways to reach. As an example, the acquired site may be a site that may be monitored via a non-invasive blood pressure monitoring device, such as an external blood pressure cuff or an external photoplethysmogram device, and the reference site may be a site that may only be directly monitored using an invasive device, such as an intraarterial blood pressure monitoring device.

In some cases, the blood pressure of a patient may vary by up to 10 mmHg or more between different arterial sites, such as between the radial artery and the middle cerebral artery. This difference may be due to the physiology of the cardiovascular system of the patient which may result in pressure drop along an arterial system or changes in blood flow profiles or patterns, the position and/or orientation of the patient's body, which may result in a different in hydrostatic pressures, or the like. For example, as the blood moves through the arterial tree, it may gradually lose pressure as energy is dissipated in forcing the blood through the vasculature. Additionally, an acquisition site blood pressure and a reference site blood pressure may differ due to, for example, vasomotion in the acquisition site arteries, which may cause an arterial line (also referred to as an a-line) to exhibit modulations in a blood pressure signal that are not present at the reference site. Such modulations may confound determination of autoregulation that is based on a relationship between a blood pressure signal and the flow signal (or a proxy of the flow signal such as an oxygen saturation signal). Hence, the blood pressure waveform generated by sensors in different locations may have a different shape and a different mean arterial pressure. Due to this difference, using an acquisition site blood pressure to determine the autoregulation status of a patient, without accounting for possible variation from the actual blood pressure at the brain, such as the middle cerebral artery blood pressure, may result in a less accurate autoregulation status determination. Thus, determining an altered blood pressure (based on an acquisition blood pressure) that is representative of the blood pressure at the brain of the patient, may enable a more accurate determination of the autoregulation status of the patient.

An autoregulation monitoring device may include processing circuitry configured to determine the cerebral autoregulation status of the patient based on the altered blood pressure value. The processing circuitry may receive a blood pressure signal indicative of a blood pressure of the patient at an acquired site and an oxygen saturation signal indicative of an oxygen saturation of the patient. In some examples, the blood pressure at the acquired site may include an arterial blood pressure (ABP) measured at the acquired site using a non-invasive blood pressure measurement, such as a blood pressure derived from external cuff or photoplethysmogram. The acquired site may include, for example, a femoral artery, a radial artery, a dorsalis pedis artery, or a brachial artery of the patient.

The processing circuitry may determine an altered blood pressure value indicative of a reference blood pressure of the patient at a reference site based on the blood pressure signal. The reference blood pressure may include, for example, an internal blood pressure that is relatively more difficult to measure by non-invasive techniques compared to the blood pressure sensed at the acquired site. For example, the reference blood pressure can include blood pressure at a middle cerebral artery, a femoral artery, or a radial artery of the patient.

The processing circuitry may determine a metric (e.g., a value) indicative of the autoregulation status of the patient based on the altered blood pressure value and the oxygen saturation signal. For example, a limit of autoregulation, such as the lower limit of autoregulation (LLA) and/or the upper limit of autoregulation (ULA), of the patient may be determined based on the altered blood pressure and an oxygen saturation of the patient. In some examples, the LLA and/or the ULA may be determined based on cerebral perfusion pressure. Cerebral perfusion pressure may be determined based on the altered blood pressure and intercranial pressure of the patient. In some examples, the processing circuitry determines the LLA and/or the ULA based on a correlation index (COx) of the blood pressure and oxygen saturation. Alternatively or additionally, the processing circuitry may determine the LLA and/or the ULA based on other parameters or correlation coefficients.

For example, in some examples, the processing circuitry may determine the LLA and/or the ULA based on a comparison of a threshold value to a change in the blood pressure (and/or oxygen saturation) of a patient over time, e.g., determining a correlation coefficient only if the change in blood pressure (and/or oxygen saturation) over time exceeds the threshold value. In some examples, as described in commonly assigned U.S. Patent Application Publication No. 2018/0014791 naming inventors Montgomery et al. and entitled, "SYSTEMS AND METHODS OF MONITORING AUTOREGULATION," which is hereby incorporated by reference in its entirety, the processing circuitry may process a blood pressure signal and an oxygen saturation signal to determine respective gradients of the signals (i.e., a blood pressure gradient and an oxygen saturation gradient) over a period of time and determine the patient's autoregulation status based on the respective gradients. As described in U.S. Patent Application Publication No. 2018/0014791, the processing circuitry may determine the autoregulation system of the patient may be impaired if the blood pressure gradient and the oxygen saturation gradient trend together (e.g., change in the same direction) over a period of time. In some cases, the processing circuitry may determine that the autoregulation system of the patient may be intact if the blood pressure gradient and the oxygen saturation gradient do not trend together (e.g., do not change in the same direction, such as change in different directions, or the blood pressure changes while the oxygen saturation remains generally stable) over the period of time.

The processing circuitry may provide a signal indicative of the autoregulation status of the patient to an output device to enable a clinician to monitor the autoregulation status of the patient. The output device can provide, for example, a visual output, an audio output, a somatosensory output, or any combination thereof, that provides information indicative of the autoregulation status of the patient to a user.

The devices, systems, and techniques of this disclosure may increase the accuracy of the presentation of an estimate of a limit of autoregulation of a patient and the presentation of an indication of the autoregulation status of the patient. For example, using the altered blood pressure may improve the determination of the autoregulation status of the patient compared to using an unaltered blood pressure because the altered blood pressure is more representative of the blood pressure at the brain of the patient than the acquisition blood pressure. The presentation of more accurate information may result in more informed decision making by the clinician, compared to autoregulation monitoring systems that do not use an altered blood pressure.

While aspects of the present disclosure are discussed with reference to ABP and oxygen saturation correlations, it should be noted that in other examples, various other signals may be determined to help evaluate a patient's autoregulation. For example, the processing circuitry may determine whether the autoregulation system of the patient is intact based on a trend between the blood oxygen saturation of the patient and the blood pressure of the patient, as described in U.S. Patent Application Publication No. 2018/0014791. For example, the processing circuitry may determine the autoregulation system of the patient is intact in response to determining the blood oxygen saturation of the patient does not trend with (e.g., change in the same direction as) a change in the patient's blood pressure and may determine the autoregulation system of the patient is intact in response to determining a change in the blood oxygen saturation trends with the change in the patient's blood pressure. An impaired autoregulation system may not adequately adjust cerebral blood flow in response to a change in the patient's blood pressure, and thus, a change in the oxygen saturation may trends with the change in the blood pressure if the autoregulation system of the patient is impaired. As discussed in U.S. Patent Application Publication No. 2018/0014791, systems and methods for monitoring autoregulation may process a blood pressure signal and an oxygen saturation signal to determine respective gradients of the signals (i.e., a blood pressure gradient and an oxygen saturation gradient) over a period of time and to determine the patient's autoregulation status based on the respective gradients.

As another example, the processing circuitry may monitor the patient's autoregulation by correlating measurements of the patient's blood pressure with measurements of the patient's blood volume (BVS) and by determining an estimate of the limit of cerebral autoregulation based on the BVS values (LABVS). The processing circuitry can determine a hemoglobin volume index (HVx) based at least in part on a linear correlation between the patient's blood pressure and blood volume. The processing circuitry can then determine an estimate of the limit of cerebral autoregulation based on the HVx values (LAHVx). The processing circuitry may also determine various other linear correlations or statistical based measures (e.g., statistical data clustering techniques) to help evaluate a patient's autoregulation status, such as a linear correlation between measurements of a patient's blood pressure and measurements of a patient's cerebral blood flow known as a mean velocity index (Mx). The processing circuitry may also determine a linear correlation between measurements of a patient's blood pressure and measurements of a patient's intracranial pressure known as a pressure reactivity index (PRx). COx may be a proxy for Mx, and HVx may be a proxy for PRx.

Other systems and techniques using similar or different parameters may be used to determine a limit of autoregulation. For example, as described in commonly assigned U.S. Patent Application Publication No. 2017/0105631 filed on Oct. 18, 2016, entitled "Systems and Method for Providing Blood Pressure Safe Zone Indication During Autoregulation Monitoring," and U.S. Patent Application Publication No. 2017/0105631 filed on Oct. 18, 2016, entitled "System and Method for Providing Blood Pressure Safe Zone Indication During Autoregulation Monitoring," systems and methods for monitoring autoregulation may use an autoregulation index to generate and display an autoregulation profile (e.g., autoregulation index values sorted into bins corresponding to different blood pressure ranges) of the patient, and generate a blood pressure (BP) safe zone (e.g., designate a blood pressure range encompassing one or more of the bins) indicative of intact autoregulation. As another example, as described in commonly assigned U.S. Patent Application Publication No. 2016/0367197 filed of Jun. 6, 2016, entitled "Systems and Methods for Reducing Signal Noise When Monitoring Autoregulation," systems and methods for monitoring autoregulation may determine linear correlations between measured physiological parameters using regression analyses, such as a least median of squares (LMS) regression method or a least trimmed squares regression method (LTS), applied to oxygen saturation measurements plotted against blood pressure measurements to determine a regression line associated with COx to ignore or exclude data outliers representative of the noise, and to utilize the remaining data to determine the COx or HVx.

FIG. 1 is a conceptual block diagram illustrating an example autoregulation monitoring system 100. Autoregulation monitoring system 100 includes processing circuitry 110, memory 120, control circuitry 122, user interface 130, sensing circuitry 140 and 142, and sensing devices 150 and 152. In the example shown in FIG. 1, user interface 130 includes display 132, input device 134, and speaker 136, which may be any suitable audio device configured to generate and output a noise. In some examples, autoregulation monitoring system 100 may be configured to determine and display the cerebral autoregulation status of a patient 101, e.g., during a medical procedure or for more long-term monitoring, such as fetal monitoring. A clinician may receive information regarding the cerebral autoregulation status of a patient via user interface 130 and adjust treatment or therapy to patient 101 based on the cerebral autoregulation status information.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Control circuitry 122 may be operatively coupled processing circuitry 110. Control circuitry 122 is configured to control an operation of sensing devices 150 and 152. In some examples, control circuitry 122 may be configured to provide timing control signals to coordinate operation of sensing devices 150 and 152. For example, sensing circuitry 140 and 142 may receive from control circuitry 122 one or more timing control signals, which may be used by sensing circuitry 140 and 142 to turn on and off respective sensing devices 150 and 152. In some examples, processing circuitry 110 may use the timing control signals to operate synchronously with sensing circuitry 140 and 142. For example, processing circuitry 110 may synchronize the operation of an analog-to-digital converter and a demultiplexer with sensing circuitry 140 and 142 based on the timing control signals.

Memory 120 may be configured to store, for example, monitored physiological parameter values (including acquired blood pressure values), altered blood pressure values, COx values, BVS values, HVx values, value(s) of an LLA and/or a ULA, determined autoregulation statuses, or any combination thereof. Memory 120 may also be configured to store data, such as associations between a first blood pressure of patient 101 at acquisition site 103 and a second blood pressure of patient 101 at reference site 105 and/or a population of patients at reference site 105 and/or threshold values. In some examples, data may be stored in memory 120 as one or more look-up tables.

In some examples, memory 120 may store program instructions, such as neural network algorithms and/or finite element algorithms. The program instructions may include one or more program modules that are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 may include a display 132, an input device 134, and a speaker 136. In some examples, user interface 130 may include fewer or additional components. User interface 130 is configured to present information to a user (e.g., a clinician). For example, user interface 130 and/or display 132 may include a monitor, cathode ray tube display, a flat panel display such as a liquid crystal (LCD) display, a plasma display, a light emitting diode (LED) display, and/or any other suitable display. In some examples, user interface 130 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 110 may be configured to present, by user interface 130, such as display 132, a graphical user interface to a user. The graphical user interface may include indications of values of one or more physiological parameters of a patient, such as, for example, blood pressure values, oxygen saturation values, information about an autoregulation status (e.g., cerebral autoregulation status), pulse rate information, respiration rate information, other patient physiological parameters, or combinations thereof via display 132. User interface 130 may also include means for projecting audio to a user, such as speaker 136.

In some examples, processing circuitry 110 may also receive input signals from additional sources (not shown), such as a user. For example, processing circuitry 110 may receive from input device 134, such as a keyboard, a mouse, a touch screen, buttons, switches, a microphone, a joy stick, a touch pad, or any other suitable input device or combination of input devices, an input signal. The input signal may contain information about patient 101, such as physiological parameters, treatments provided to patient 101, or the like. Additional input signals may be used by processing circuitry 110 in any of the determinations or operations it performs in accordance with processing circuitry 110.

In some examples, if processing circuitry 110 determines that the autoregulation status of patient 101 is impaired, then processing circuitry 110 may present a notification indicating the impaired cerebral autoregulation status. The notification may include a visual, audible, tactile, or somatosensory notification (e.g., an alarm signal) indicative of an autoregulation status of patient 101. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., communication interface 290 shown in FIG. 2).

Sensing circuitry 140 and 142 may be configured to receive physiological signals sensed by respective sensing devices 150 and 152 and communicate the physiological signals to processing circuitry 110. Sensing devices 150 and 152 may include any sensing hardware configured to sense a physiological parameter of a patient, such as, but not limited to, one or more electrodes, optical receivers, blood pressure cuffs, or the like. The sensed physiological signals may include signals indicative of physiological parameters from a patient, such as, but not limited to, blood pressure, regional oxygen saturation, blood volume, heart rate, and respiration. For example, sensing circuitry 140 and 142 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof.

In some examples, sensing circuitry 140 and 142 and/or processing circuitry 110 may include signal processing circuitry 112 configured to perform any suitable analog conditioning of the sensed physiological signals. For example, sensing circuitry 140 and 142 may communicate to processing circuity 110 an unaltered (e.g., raw) signal. Processing circuitry 110, e.g., signal processing circuitry 112, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of signal processing circuitry 112 to convert the conditioned analog signals into digital signals. In some examples, signal processing circuitry 112 may operate on the analog or digital form of the signals to separate out different components of the signals. In some examples, signal processing circuitry 112 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 112 may decrease the number of samples in the digital detector signals. In some examples, signal processing circuitry 112 may remove dark or ambient contributions to the received signal. Additionally or alternatively, sensing circuitry 140 and 142 may include signal processing circuitry 112 to modify one or more raw signals and communicate to processing circuity 110 one or more modified signals.

Oxygen saturation sensing device 150 is configured to generate an oxygen saturation signal indicative of blood oxygen saturation within the venous, arterial, and/or capillary systems within a region of patient 101. For example, oxygen saturation sensing device 150 may be configured to be placed on the skin of patient 101 to determine regional oxygen saturation of a particular tissue region, e.g., the frontal cortex or another cerebral location of patient 101. Oxygen saturation sensing device 150 may include emitter 160 and detector 162. Emitter 160 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 150, sensing circuitry 140, control circuitry 122, and/or processing circuitry 110) may provide a light drive signal to drive emitter 160 and to cause emitter 160 to emit light. In some examples, the LEDs of emitter 160 emit light in the range of about 600 nanometers (nm) to about 1000 nm. In a particular example, one LED of emitter 160 is configured to emit light at about 730 nm and the other LED of emitter 160 is configured to emit light at about 810 nm. Other wavelengths of light may be used in other examples.

Detector 162 may include a first detection element positioned relatively "close" (e.g., proximal) to emitter 160 and a second detection element positioned relatively "far" (e.g., distal) from emitter 160. In some examples, the first detection elements and the second detection elements may be chosen to be specifically sensitive to the chosen targeted energy spectrum of light source 160. Light intensity of multiple wavelengths may be received at both the "close" and the "far" detector 162. For example, if two wavelengths are used, the two wavelengths may be contrasted at each location and the resulting signals may be contrasted to arrive at an oxygen saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). In operation, light may enter detector 162 after passing through the tissue of patient 101, including skin, bone, other shallow tissue (e.g., non-cerebral tissue and shallow cerebral tissue), and/or deep tissue (e.g., deep cerebral tissue). Detector 162 may convert the intensity of the received light into an electrical signal. The light intensity may be directly related to the absorbance and/or reflectance of light in the tissue. Surface data from the skin and skull may be subtracted out, to generate an oxygen saturation signal for the target tissues over time.

Oxygen saturation sensing device 150 may provide the oxygen saturation signal to processing circuitry 110 or to any other suitable processing device to enable evaluation of an autoregulation status of patient 101. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation.".

In operation, blood pressure sensing device 152 and oxygen saturation sensing device 150 may each be placed on the same or different parts of the body of patient 101. For example, blood pressure sensing device 152 and oxygen saturation sensing device 150 may be physically separate from each other and may be separately placed on patient 101. As another example, blood pressure sensing device 152 and oxygen saturation sensing device 150 may in some cases be part of the same sensor or supported by a single sensor housing. For example, blood pressure sensing device 152 and oxygen saturation sensing device 150 may be part of an integrated oximetry system configured to non-invasively measure blood pressure (e.g., based on time delays in a plethysmography (PPG) signal) and regional oxygen saturation. One or both of blood pressure sensing device 152 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example autoregulation monitoring system 100 is shown in FIG. 1, the components illustrated in FIG. 1 are not intended to be limiting. Additional or alternative components and/or implementations may be used in other examples.

Blood pressure sensing device 152 may be any sensor or device configured to generate a blood pressure signal indicative of an acquisition blood pressure of patient 101 at acquisition site 103. For example, blood pressure sensing device 152 may include a blood pressure cuff configured to non-invasively monitoring blood pressure, a sensor configured to noninvasively generate a PPG signal, or an arterial line for invasively monitoring blood pressure in an artery of patient 101. In some examples, the blood pressure signal may include at least a portion of a waveform of the acquisition blood pressure. In some examples, acquisition site 103 may include at least one of a femoral artery of patient 101, a radial artery of patient 101, a dorsalis pedis artery of patient 101, a brachial artery of patient 101, or combinations thereof. In some examples, blood pressure sensing device 152 may include a plurality of blood pressure sensing devices. For example, each blood pressure sensing device of the plurality of blood pressure sensing devices may be configured to obtain a respective blood pressure of patient 101 at a respective acquisition site of a plurality of acquisition sites. The plurality of acquisition sites may include similar or different arteries of patient 101.

In some examples, blood pressure sensing device 152 may include one or more pulse oximetry sensors. The acquisition blood pressure may be derived by processing time delays between two or more characteristic points within a single PPG signal obtained from a single pulse oximetry sensor. Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring.". In other cases, the blood pressure of patient 101 may be continuously, non-invasively monitored via multiple pulse oximetry sensors placed at multiple locations on patient 101. As described in commonly assigned U.S. Pat. No. 6,599,251, issued Jul. 29, 2003, and entitled "Continuous Non-invasive Blood Pressure Monitoring Method and Apparatus." multiple PPG signals may be obtained from the multiple pulse oximetry sensors, and the PPG signals may be compared against one another to estimate the blood pressure of patient 101.

Regardless of its form, blood pressure sensing device 152 may be configured to generate a blood pressure signal (also referred to herein as an acquired blood pressure signal) indicative of an acquisition blood pressure of patient 101 at acquisition site 103 (e.g., arterial blood pressure) over time. In examples in which blood pressure sensing device 152 includes a plurality of blood pressure sensing devices, the blood pressure signal may include a plurality of blood pressure signals, each indicative of a blood pressure of patient 101 at a respective acquisition site. Blood pressure sensing device 152 may provide the blood pressure signal to sensing circuitry 142, processing circuitry 110, or to any other suitable processing device to enable evaluation of the autoregulation status of patient 101.

Processing circuitry 110 may be configured to receive one or more signals generated by sensing devices 150 and 152 and sensing circuitry 140 and 142. The physiological signals may include a signal indicating blood pressure and/or a signal indicating oxygen saturation. Processing circuitry 110 may be configured to determine an altered blood pressure value based on the blood pressure signal. The altered blood pressure value may be indicative of a reference blood pressure of patient 101 at reference site 105 that is different from acquired site 103. For example, the reference blood pressure may indicate a blood pressure of patient 101 at reference site 105 of patient 101 contemporaneous with (e.g., at the same moment in time) the measured acquisition blood pressure.

In some examples, reference site 105 may include a site at which the blood pressure is more representative of the blood pressure at the brain of patient 101 compared to the acquisition blood pressure. For example, acquisition site 103 may include a radial artery, a dorsalis pedis artery, or a brachial artery and reference site 105 may include the middle cerebral artery or the femoral artery of patient 101, which may require invasive techniques to measure directly or may be more difficult to acquire by noninvasive techniques than the blood pressure at acquisition site 103. In this way, an acquisition blood pressure may be used to predict the actual blood pressure at the brain of patient 101 without subjecting patient 101 to invasive blood pressure measurement techniques. Using noninvasive blood pressure measurements that are relatively easier to acquire also may reduce time and effort by clinicians in establishing an indication of blood pressure at the brain of patient 101. Moreover, two or more acquisition blood pressures may be used to independently determine two altered blood pressures that then may be compared to more accurately predict the actual blood pressure at the brain of patient 101. Blood pressure at the brain of patient 101 may be more suitable for determining an autoregulation status of patient 101 due to, for example, the algorithms employed by processing circuitry 110 to determine the autoregulation status of patient 101. The algorithms employed by processing circuitry 110 to determine the autoregulation status of patient 101 may not account for different acquisition sites 103 and may be based on blood pressures sensed at one particular site, e.g., the reference site. Thus, by "translating" acquired blood pressure measurements to the reference blood pressure measurements, processor 110 may more accurately determine an autoregulation status of patient 101.

In some examples, processing circuitry 110 is configured to determine the altered blood pressure value based on mapping the acquisition blood pressure to the reference blood pressure. The acquisition blood pressure may include a waveform of the acquisition blood pressure measured at acquisition site 103. Mapping may include transforming one or more positions of the waveform (e.g., amplitudes) of the acquisition blood pressure (e.g., including both pressure and relative timing) to a corresponding one or more positions of the waveform of the reference blood pressure at reference site 105 (e.g., including both pressure and relative timing). In other words, in this example, the reference blood pressure at reference site 105 includes the actual unmeasured blood pressure at reference site 105, whereas the altered blood pressure includes the predicted (e.g., determined) blood pressure at reference site 105. The one or more portions of the waveform may include any discrete point on the waveform or sets of points on the waveform, such as, for example, at or near any of the systolic upstroke, the systolic peak pressure, the systolic decline, the dicrotic notch, the diastolic runoff, and/or the end-diastolic pressure.

In some examples, processing circuitry 110 is configured to map the acquisition blood pressure to the reference blood pressure in order to determine the altered blood pressure using at least one of a physiological model, a neural network algorithm, a population-based model, a finite element model, or other algorithm to associate a first blood pressure of patient 101 at acquisition site 103 with a second blood pressure of patient 101 at reference site 105. The physiological model, the neural network algorithm, the population-based model, the finite element model, or other algorithm may define a relationship between the acquisition blood pressure and the reference blood pressure, such that the reference blood pressure can be determined based on the acquired blood pressure. By associating a first blood pressure of patient 101 at acquisition site 103 with a second blood pressure of patient 101 at reference site 105, processing circuitry 110 may determine the altered blood pressure value indicative of a reference blood pressure of patient 101 at reference site 105 based on the blood pressure signal (e.g., the acquisition blood pressure).

In some examples, mapping may account for physiological parameters that may affect the acquisition blood pressure, the reference blood pressure, or portions of the waveforms thereof. In some examples, mapping may account for differences in hydrostatic pressure between a first blood pressure of patient 101 at acquisition site 103 and a second blood pressure of patient 101 at reference site 105. For example, the position of patient 101, such as supine, prone, right lateral, left lateral, Fowler's, Trendelenberg, or other positions, may affect the hydrostatic pressure at or between the first blood pressure of patient 101 at acquisition site 103 and the second blood pressure of patient 101 at reference site 105. Mapping may use a correction factor that is based on (e.g., equal or nearly equal) to the difference in hydrostatic pressures between the first blood pressure of patient 101 at acquisition site 103 and the second blood pressure of patient 101 at reference site 105 for a given position of patient 101 or the difference in hydrostatic pressures between the first blood pressure of patient 101 at acquisition site 103 (or the second blood pressure of patient 101 at reference site 105) in a first position of patient 101 and a second position of patient 101. By accounting for hydrostatic pressure differences, mapping may more accurately determine the altered blood pressure value compared to systems and techniques that do not account for hydrostatic pressure differences.

In some examples, mapping may account for morphological differences in the waveforms of the first blood pressure of patient 101 at acquisition site 103 and the second blood pressure of patient 101 at reference site 105. Morphological differences may include, for example, the shape of the wave form and/or features of the waveform, such as the systolic upstroke, the systolic peak pressure, the systolic decline, the dicrotic notch, the diastolic runoff, and/or the end-diastolic pressure. For example, mapping may identify a first shape and/or feature of the first blood pressure that is unique to acquisition site 103, e.g., a femoral artery, a radial artery, a dorsalis pedis artery, or a brachial artery of patient 101. Mapping may match the shape and/or the feature to an expected shape and/or features of the second blood pressure that is unique to reference site 105, e.g., a femoral artery or a middle cerebral artery of patient 101. Accounting for the morphological differences in the waveforms may include mapping a selected feature of the first blood pressure to a corresponding feature of the second blood pressure, e.g., the systolic upstroke, the systolic peak pressure, the systolic decline, the dicrotic notch, the diastolic runoff, and/or the end-diastolic pressure. By accounting for morphological differences in the waveforms, mapping may more accurately predict the altered blood pressure value compared to systems and technique that do not account for morphological difference in the waveforms.

In some examples, processing circuitry 110 may determine a relationship between the acquisition blood pressure and the reference blood pressure using a physiological model based on a predetermined association between a first blood pressure of patient 101 at acquisition site 103 and a second blood pressure of patient 101 at reference site 105. For example, processing circuitry 110 may retrieve from memory 120 patient specific data including one or more first blood pressure values that was measured at acquisition site 103 on patient 101, one or more second blood pressure values that was measured at reference site 105 on patient (measured contemporaneous with the first blood pressure) at substantially the same time (e.g., the exact same time or nearly the same time to the extent permitted by the sensing devices), and/or a predetermined association (e.g., relationship) between the first blood pressure and the second blood pressure.

In some examples, the physiological model may include one or more look-up tables and/or one or more equations. An example look-up table may include one or more first blood pressures of patient 101 measured at acquisition site 103 and one or more second blood pressures of patient 101 measured (contemporaneously with the first blood pressures) at reference site 105. An example equation may be defined by the parameterization of the one or more first blood pressure values of patient 101 measured at acquisition site 103 and one or more second blood pressure values of patient 101 measured (contemporaneously with the first blood pressures) at reference site 105. Using patient specific data may enable processing circuitry 110 to more accurately determine the association between the first and second blood pressures compared to using other data, such as associations based on first and second blood pressures from a pool of different patients.

Memory 120 may store the look-up table, equation, or other physiological model. Processing circuitry 110 may be configured to retrieve from memory 120 the look-up table values to determine the reference blood pressure based on the blood pressure signal by, for example, looking up the blood pressure value indicated by the blood pressure signal to retrieve the associated reference blood pressure. In addition to or instead of the look-up table, processing circuitry 110 may retrieve from memory 120 one or more equations to apply to the blood pressure value indicated by the blood pressure signal to determine the corresponding reference blood pressure. By using the physiological model, processing circuitry 110 may determine the altered blood pressure based on a predetermined association of the acquisition blood pressure and the reference blood pressure for the particular patient.

In some examples, processing circuitry 110 may determine a relationship between the acquisition blood pressure and the reference blood pressure using a population-based model. The population-based model may be based on a predetermined association (e.g., relationship) between a first blood pressure of a population of patients at acquisition site 103 and a second blood pressure of the population of patients at reference site 105. For example, the population-based model may include one or more look-up tables and/or one or more equations based on data collected from a population of two or more patients (e.g., a plurality of members of the population). Processing circuitry 110 may use the look-up table and/or equation of the population-based model in the same manner as described above with respect to the physiological model. Using data collected from a population of two or more patients may enable processing circuitry 110 to determine the association between the first and second blood pressures without patient specific data that may otherwise required invasive blood pressure monitoring.

In some examples, in addition to the one or more first blood pressures of each member of the population measured at acquisition site 103 and one or more second blood pressures of each member of the population measured (contemporaneously with the first blood pressures) at reference site 105, the look-up table may include demographic data related to each member of the population. The demographic data (e.g., demographic indicators) may include, for example, age, gender, and existing medical conditions. The demographic data may be used to identify associations of the first blood pressure and the second blood pressure from members of the population that match (e.g., substantially resemble) the demographic data of patient 101. For example, a clinician may select a subset of the population-based data having demographic indicators that match the demographic indicators of patient 101. Additionally or alternatively, a clinician may input patient's demographic data into processing circuitry 110, and processing circuitry 110 may be configured to automatically select a subset of the population-based data having demographic indicators that match the demographic indicators of patient 101. Similarly, the one or more equations may include one or more indicators associated with the demographic data such that a clinician or processing circuitry 110 may select one or more equations associated with members of the population that match the demographic data of patient 101. By using the population-based model, processing circuitry 110 may determine the altered blood pressure of patient 101 based on an association of the acquisition blood pressure and the reference blood pressure derived from members of a population having similar demographic characteristics as patient 101. Using demographic data may enable processing circuity 110 to filter population-based data to more accurately determine an association between the first and second blood pressures for patient 101 compared to using population-based data without filtering the data based on demographic indicators.

In some examples, one or more equations representing a physiological model and/or population-based model may include complex relationships between input variables associated with patient 101, such as, for example, an acquisition blood pressure or blood pressure signal, a location of acquisition site 103, a location of reference site 105, an oxygen saturation, demographic data, a relative position of the body or limbs of patient 101, and other physiological data, and output variables, such as, for example, a reference blood pressure or an altered blood pressure and reference site 105. The complex relationships of input variable and output variables may make determining the altered blood pressure computationally intensive, such that it may not be practical to rely on the physiological model and/or population-based model for real-time determination of the altered blood pressure. In some examples, processing circuitry 110 may be configured to determine the altered blood pressure value by determining a relationship between the acquisition blood pressure and the reference blood pressure using a neural network algorithm.

A neural network algorithm, or artificial neural network, may include a trainable or adaptive algorithm utilizing nodes that define rules. For example, a respective node of a plurality of nodes may utilize a function, such as a non-linear function or if-then rules, to generate an output based on a input. A respective node of the plurality of nodes may be connected to one or more different nodes of the plurality of nodes along an edge, such that the output of the respective node includes the input of the different node. The functions may include parameters that may be determined or adjusted using a training set of inputs and desired outputs, such as, for example, a predetermined association between one or more first blood pressures of patient 101 or a population of patients measured at acquisition site 103 and one or more second blood pressures of patient 101 or a population of patients measured (contemporaneously with the first blood pressures) at reference site 105, along with a learning rule, such as a back-propagation learning rule. The back-propagation learning rule may utilize one or more error measurement comparing the desired output to the output produced by the neural network algorithm to train the neural network algorithm by varying the parameters to minimize the one or more error measurements.

An example neural network includes a plurality of nodes, at least some of the nodes having node parameters. An input including at least the first blood pressure of patient 101 at acquisition site 103 may be input to a first node of the neural network algorithm. In some examples, the input may include a plurality of inputs, each input into a respective node. The first node may include a function configured to determine an output based on the input and one or more adjustable node parameters. In some examples, the neural network may include a propagation function configured to determine an input to a subsequent node based on the output of a preceding node and a bias value. In some examples, a learning rule may be configured to modify one or more node parameters to produce a favored output. For example, the favored output may be constrained by one or more threshold values and/or to minimize one or more error measurements. The favored output may include an output of a single node, a set of nodes, or the plurality of nodes. In some examples, the favored output includes the second blood pressure of patient 101 at reference site 105, e.g., the altered blood pressure value.

The neural network algorithm may iteratively modify the node parameters until the output includes the favored output. In this way, processing circuitry 100 may be configured to iteratively evaluating outputs of the neural network algorithm and iteratively modifying at least one of the node parameters based on the evaluation of the outputs of the neural network algorithm to determine the altered blood pressure value based on the modified neural network algorithm. In some examples, a neural network algorithm may enable processing circuitry 110 to more accurately determine the altered blood pressure value by using more associations of the first blood pressures measured at acquisition site 103 and second blood pressures measured at reference site 105 compared to other techniques and/or reduce computational time and/or power required to determine the altered blood pressure value.

In some examples, processing circuitry 110 may determine a relationship between the acquisition blood pressure and the reference blood pressure using a finite element model. The finite element model may be based on a plurality of finite elements configured to model an association between the first blood pressure of patient 101 at acquisition site 103 and the second blood pressure of patient 101 at reference site 105. For example, the finite element model may include a plurality of finite elements. A respective finite element of the plurality of finite elements may include one or more equations associating a region of the waveform of the acquisition blood pressure (e.g., pressure and relative timing) to a corresponding region of a waveform of the acquisition blood pressure (e.g., pressure and relative timing). For example, the region of the waveform may include discrete points on the waveform or sets of points on the waveform, such as, for example, at or near the systolic upstroke, systolic peak pressure, systolic decline, dicrotic notch, diastolic runoff, and/or end-diastolic pressure. In some examples, the one or more equations of each finite element may be defined by the parameterized relation of the one or more first blood pressure values of patient 101 measured at acquisition site 103 and one or more second blood pressure values of patient 101 or a population of patient measured (contemporaneously with the first blood pressures) at reference site 105, as discussed above. After determining a corresponding region of a waveform of the reference blood pressure for each finite element, the plurality of finite elements may be systematically recombined to determine the waveform of the altered blood pressure including the altered blood pressure value.

After determining the altered blood pressure value, processing circuitry 110 may determine a metric (e.g., a numerical value or qualitative information) indicative of the autoregulation status of patient 101 based on the altered blood pressure value and the oxygen saturation signal. For example, processing circuitry 110 may determine a correlation index (e.g., COx, HVx) or other measure of autoregulation, such as based on co-trending of blood pressure and blood oxygen saturation, (e.g., based on a comparison of blood pressure gradients and oxygen saturation gradients), based on the determined altered blood pressure value and the measured oxygen saturation value. In other examples, processing circuitry 110 may determine the correlation index based on additional or alternative physiological parameters (e.g., physiological signals), such as, for example, a blood volume value or a gradients measure. Processing circuitry 110 may then determine an estimate of an LLA based on the lowest blood pressure value at which the expected value of COx is less than a threshold value, such as 0.5, 0.4, 0.3, 0.2, 0.1, or 0.0. Using this threshold value, processing circuitry 110 can determine where there is a distinct change in a correlation between the altered blood pressure and the oxygen saturation, such as a oxygen saturation versus altered blood pressure curve. This distinct change may correspond to a distinct step down in the plot of COx or HVx versus blood pressure.

Similarly, processing circuitry 110 may determine an estimate of a ULA based on the highest blood pressure value at which the expected value of COx is less than a threshold value. Additional example details of determining limits of autoregulation (Las) and cerebral autoregulation status may be found in commonly assigned U.S. Patent Application Publication No. 2018/0014791, filed on Jul. 13, 2017, entitled "Systems and Methods of Monitoring Autoregulation"; commonly assigned U.S. Patent Application Publication No. 2018/0049649 filed on Aug. 1, 2017, "System and Method for Identifying Blood Pressure Zones During Autoregulation Monitoring"; commonly assigned U.S. Patent Application Publication No. 2016/0367197 filed on Dec. 22, 2016, entitled "Systems and Methods of Reducing Signal Noise When Monitoring Autoregulation"; and commonly assigned U.S. patent application Ser. No. 15/962,438 filed on Apr. 25, 2018, entitled "Determining Changes to Autoregulation." In some examples, processing circuitry 110 may determine that a patient has intact autoregulation in response to determining that the blood pressure of patient 101 is greater than an LLA and less than an ULA (e.g., the blood pressure is between the limits of autoregulation).

Once processing circuitry 110 has determined the metric indicative of the autoregulation status of patient 101, processing circuitry 110 may provide information indicative of the autoregulation status of patient 101 to an output device, such as user interface 130. Processing circuitry 101 generates the information based on the metric indicative of the autoregulation status. In some examples, user interface 130, for example, display 132, may present a graphical user interface that includes information indicative of a determined autoregulation status of patient 101 (e.g., an indication of an impaired autoregulation state). In some examples, the indication of autoregulation status may include text, colors, and/or audio presented to a user. Processing circuitry 110 may be further configured to present an indication of one or more limits of autoregulation, blood pressure(s), oxygen saturation(s), or the like, on the graphical user interface. In addition to or instead of the graphical user interface, processor circuitry 110 may be configured to generate and present information indicative of a determined autoregulation status of patient 101 via speaker 136. For example, in response to detecting an impaired autoregulation state of patient 101, processing circuitry 110 may generate an audible alert via speaker 136.

In some examples, autoregulation monitoring device 100, e.g., processing circuitry 110 or user interface 130, may include a communication interface to enable autoregulation monitoring device 100 to exchange information with external devices. The communication interface may include any suitable hardware, software, or both, which may allow autoregulation monitoring device 100 to communicate with electronic circuitry, a device, a network, a server or other workstations, a display, or any combination thereof. For example, processing circuitry 100 may receive acquisition blood pressure values and/or oxygen saturation values from an external device via the communication interface.

The components of autoregulation monitoring device 100 that are shown and described as separate components are shown and described as such for illustrative purposes only. In some examples the functionality of some of the components may be combined in a single component. For example, the functionality of processing circuitry 110 and control circuitry 122 may be combined in a single processor system. Additionally, in some examples the functionality of some of the components of autoregulation monitoring device 100 shown and described herein may be divided over multiple components. For example, some or all of the functionality of control circuitry 122 may be performed in processing circuitry 110, or sensing circuitry 140 and 142. In other examples, the functionality of one or more of the components may be performed in a different order or may not be required.

Figure 2:
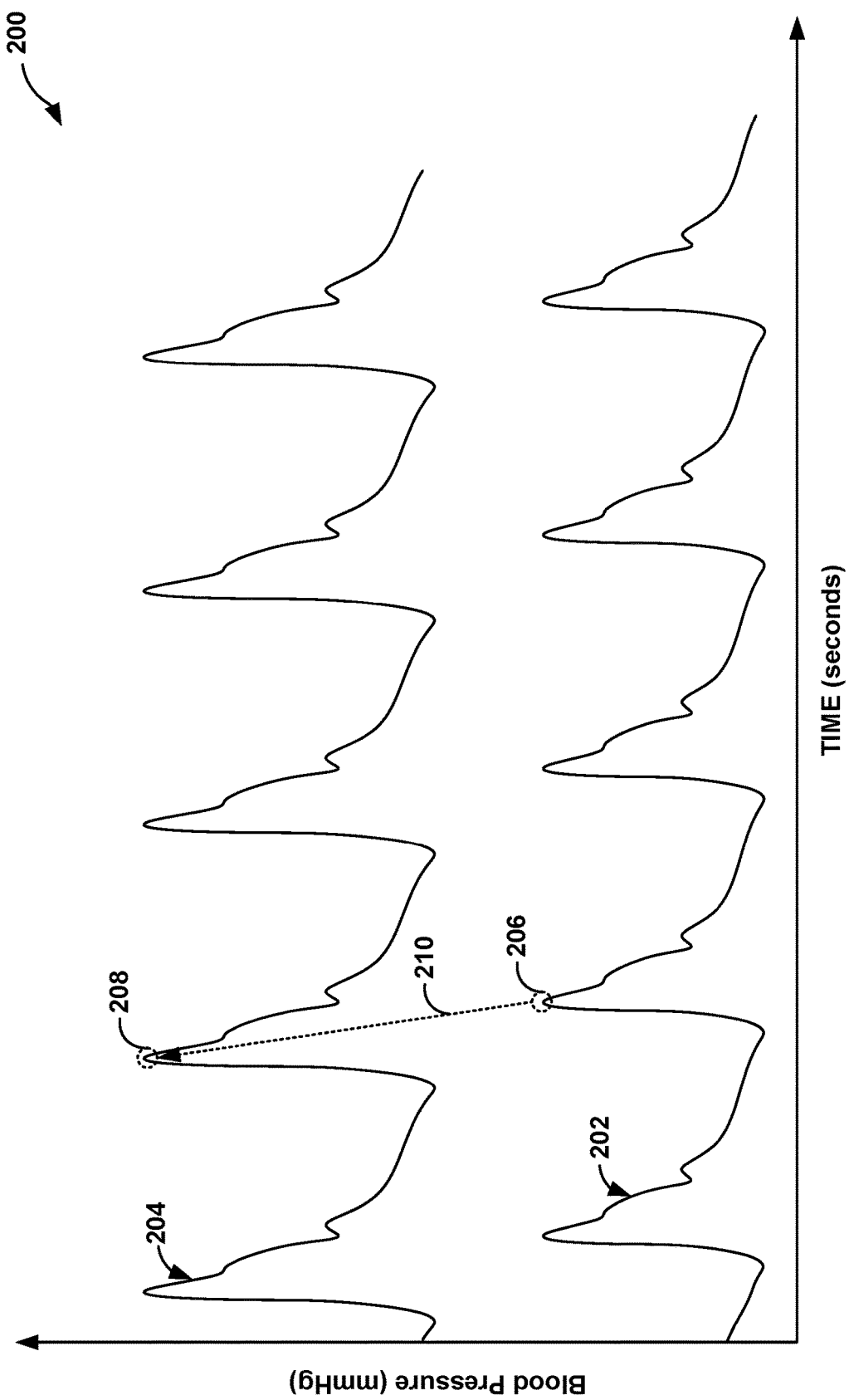
FIG. 2 illustrates an example graph of blood pressure versus time representing an example mapping of an acquisition blood pressure from a radial artery of a patient to an altered blood pressure indicative of a reference blood pressure at a femoral artery of the patient.

FIG. 2 illustrates an example graph 200 of blood pressure versus time representing mapping of an acquisition blood pressure from a radial artery of a patient to an altered blood pressure indicative of a reference blood pressure at a femoral artery of patient 101. In some examples, graph 200 or a similar graphic may be displayed to a clinician, for example, by processing circuitry 110 via user interface 130. In the example shown in FIG. 2, the acquisition blood pressure is represented as radial artery blood pressure waveform 202 and the altered blood pressure is represented as femoral artery blood pressure waveform 204.

Waveforms 202 and 204 may have specific shapes and/or features that include discrete points or sets of points on the waveform, such as, for example, the systolic upstroke, the systolic peak pressure, the systolic decline, the dicrotic notch, the diastolic runoff, the end-diastolic pressure, or any other identifiable region of the waveform. As discussed above, mapping, e.g., by processing circuitry 110, may include identifying a first shape and/or feature of the acquisition blood pressure (e.g., first blood pressure) that is unique to acquisition site 103 (e.g., the radial artery). For example, as part of the mapping process, processing circuitry 110 may identify the apex of systolic peak 206. In some examples, mapping may include identifying a plurality of shapes and/or features. Mapping may include transforming (e.g., translation or other affine transform) the shape and/or the feature of the first blood pressure to an expected shape and/or features of the second blood pressure that is unique to reference site 105, e.g., the femoral artery.

For example, to transform identified systolic peak 206 of radial blood pressure waveform 202 to systolic peak 208 of (predicted) femoral blood pressure waveform 204, processing circuitry 110 use a predetermined association to determine a transformation of the time and pressure of systolic peak 206 (e.g., transformation 210) to result in systolic peak 208 of femoral blood pressure waveform 204. As discussed above, transformation 210 is based on an association that may be determined from a physiological model, a population-based model, a neural network algorithm, a finite element analysis model or other algorithms or models. As illustrated, transformation 210 includes a temporal shift, e.g., femoral systolic peak 208 may occur before radial systolic peak 206, and an amplitude shift, e.g., femoral systolic peak 208 may have a greater pressure than radial systolic peak 206. In some examples, mapping may include iterative transformations of a plurality of waveform shapes and/or features to effectively shift waveform 202 to waveform 204.

Figure 3:
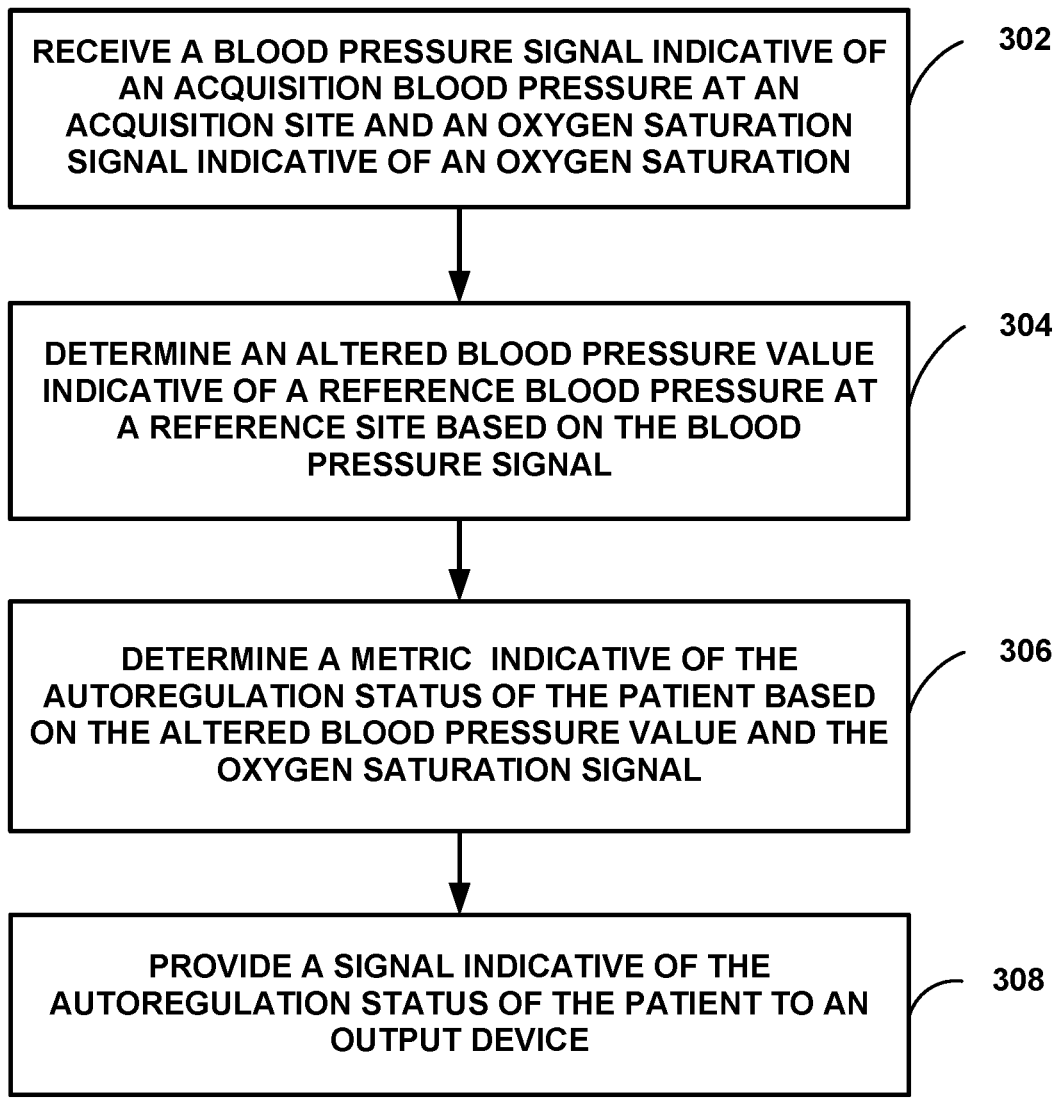
FIG. 3 is a flow diagram illustrating an example method of monitoring the autoregulation status of a patient.

FIG. 3 is a flow diagram illustrating an example method of monitoring the autoregulation status of a patient. Although FIG. 3 is described with respect to processing circuitry 110 of autoregulation monitoring system 100 (FIG. 1), in other examples, different processing circuitry, alone or in combination with processing circuitry 110, may perform any part of the technique of FIG. 3. The technique illustrated in FIG. 3 includes receiving, by processing circuitry 110, a blood pressure signal indicative of an acquisition blood pressure of patient 101 at acquisition site 103 and an oxygen saturation signal indicative of an oxygen saturation of patient 101 (302). In some examples, receiving the blood pressure signal (302) includes non-invasively measuring the blood pressure of patient 101 at acquisition site 103, e.g., using external cuff or photoplethysmogram, as discussed above. The acquired site may include at least one of a femoral artery, a radial artery, a dorsalis pedis artery, or a brachial artery of patient 101. In some examples, the blood pressure signal may include a plurality of blood pressure signals. Each blood pressure signal of the plurality of blood pressure signals may be indicative of a blood pressure of patient 101 at a respective acquisition site of a plurality of acquisition sites.

The technique illustrated in FIG. 3 also includes determining, by processing circuitry 110, an altered blood pressure value indicative of a reference blood pressure of patient 101 at reference site 105 based on the blood pressure signal (304). As discussed above, determining the altered blood pressure value (304) may include determining the altered blood pressure value based on mapping the acquisition blood pressure to the reference blood pressure. For example, as described below in reference to FIGS. 4-7, processing circuitry 100 may map the acquisition blood pressure to the reference blood pressure using at least one of a physiological model, a population-based model, a neural network algorithm, or a finite element model to associate a first blood pressure of patient 101 at acquisition site 103 with a second blood pressure of patient 101 at reference site 105. In some examples, reference site 105 may include at least one of a femoral artery or a middle cerebral artery. For example, a blood pressure of patient 101 at the femoral artery or the middle cerebral artery may be representative of the blood pressure at the brain of patient 101, and blood pressure at the brain of patient 101 may provide a more accurate blood pressure for purposes of determining an autoregulation status of patient 101.

In some examples, the mapping accounts for differences in hydrostatic pressure between the first blood pressure of patient 101 at acquisition site 103 and the second blood pressure of patient 101 at reference site 105. For example, as discussed above, mapping may use correction factor equal to the difference in hydrostatic pressures between an acquisition blood pressure (e.g., a first blood pressure) of patient 101 at acquisition site 103 and a reference blood pressure (e.g., a second blood pressure) of patient 101 at reference site 105 for a given position of patient 101 or the difference in hydrostatic pressures between the first blood pressure of patient 101 at acquisition site 103 (or the second blood pressure of patient 101 at reference site 105) in a first position of patient 101 and a second position of patient 101. In this way, the technique may correct for a difference in hydrostatic pressure between the first blood pressure of patient 101 at acquisition site 103 and the second blood pressure of patient 101 at reference site 105

In some examples, the mapping accounts for morphological differences in the waveforms of the first blood pressure of patient 101 at acquisition site 103 and the second blood pressure of patient 101 at reference site 105. For example, as discussed above, accounting for the morphological differences in the waveforms may include mapping a selected feature of the first blood pressure to a corresponding feature of the second blood pressure. By accounting for morphological differences in the waveforms, the technique may more accurately predict the altered blood pressure value compared to systems and technique that do not account for morphological difference in the waveforms.

In examples in which the blood pressure signal includes a plurality of blood pressure signals, determining the altered blood pressure value indicative of a reference blood pressure of patient 101 at reference site 105 (304) may be based on the plurality of blood pressure signals. For example, processing circuitry 110 may determine for each respective blood pressure signal a respective altered blood pressure value of a plurality of altered blood pressure values. In some examples, processing circuitry may determine an average of the plurality of altered blood pressure values, such as a mean or a weighted-average. Additionally or alternatively, processing circuitry 110 may determine an average of the plurality of blood pressure signals, such as a mean or a weighted-average, and determine an altered blood pressure value indicative of a reference blood pressure of patient 101 at reference site 105 (304) may be based on the average of the plurality of blood pressure signals.

The technique illustrated in FIG. 3 also includes determining, by processing circuitry 110, a metric indicative of the autoregulation status of patient 101 based on the altered blood pressure value and the oxygen saturation signal (306). In some examples, determining the METRIC indicative of the autoregulation status of patient 101 (306) may include determining at least one of an LLA or a ULA based on the altered blood pressure value. For example, as discussed above, processing circuitry 110 may determine a correlation index (e.g., COx, HVx) based on the determined altered blood pressure value and the measured oxygen saturation value, or additional or alternative physiological parameters, and then determine an estimate of an LLA based on the lowest blood pressure value at which the expected value of COx is less than a threshold value and/or a ULA based on the highest blood pressure value at which the expected value of COx is greater than a threshold value.

The technique illustrated in FIG. 3 also includes providing, by processing circuitry 110, a signal indicative of the autoregulation status of patient 101 to an output device, such as user interface 130 (308). For example, as discussed above, display 132 and/or speaker 136 may present to a clinician a graphical user interface that includes an indicator of autoregulation status, such as text, colors, and/or audio. Processing circuitry 110 may be further configured to present an indication of one or more limits of autoregulation, blood pressure(s), oxygen saturation(s), or the like, on the graphical user interface.

Figure 4:
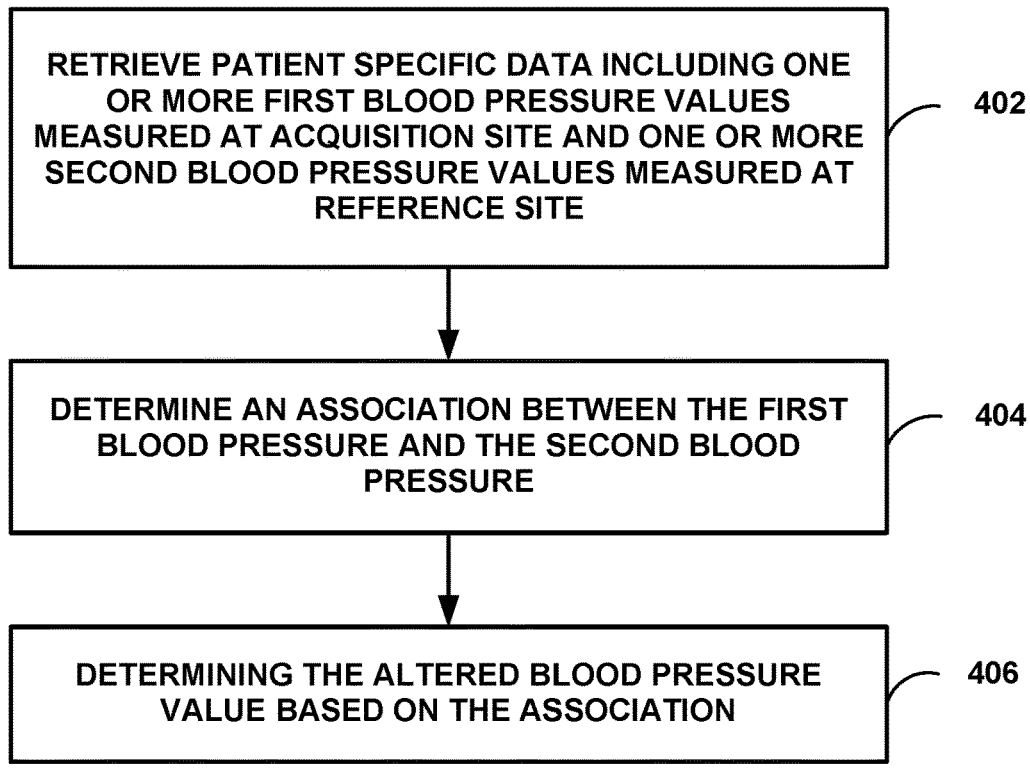
FIGS. 4-7 are flow diagrams illustrating example techniques for determining a reference site blood pressure based on an acquisition site blood pressure.

FIGS. 4-7 are flow diagrams illustrating example techniques for determining reference site 105 blood pressure based on acquisition site 103 blood pressure. In some examples, determining the altered blood pressure (304) includes using a physiological model, as illustrated in FIG. 4. In the technique illustrated in FIG. 4, processing circuitry 110 retrieves, e.g., from memory 120 or from a remote database, patient specific data including one or more first blood pressure values measured at acquisition site 103 on patient 101 and one or more second blood pressure values measured at reference site 105 on patient (measured contemporaneous with the first blood pressure) (402).

The technique illustrated in FIG. 4 also includes determining, by processing circuitry 110, an association (e.g., relationship) between the first blood pressure and the second blood pressure (404). For example, determining the association may include parameterizing two or more sets of first blood pressures and second blood pressure measured contemporaneously. In some examples, the technique may include storing in memory 120 a look-up table, equation, or other physiological model based on the determined association. In some examples, rather than determining the association, processing circuitry 110 may retrieve, e.g., from memory 120 or from a remote database, the association (e.g., relationship) between the first blood pressure and the second blood pressure, such as a stored look-up table, equation, or other physiological model. Processing circuitry 110 may determine the altered blood pressure value based on the physiological model based association (406). In this way, the technique illustrated in FIG. 4 includes determining a relationship between the acquisition blood pressure and the reference blood pressure using a physiological model based on a predetermined association between a first blood pressure of patient 101 at acquisition site 103 and a second blood pressure of patient 101 at reference site 105.

Figure 5:
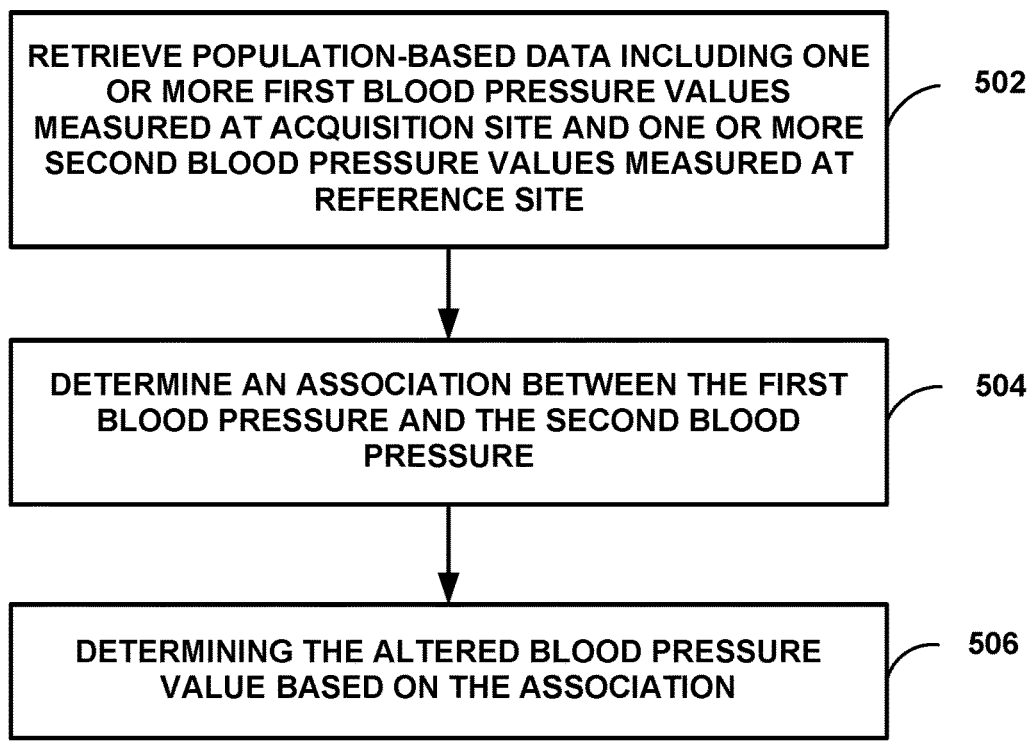

In some examples, determining the altered blood pressure (304) may include using a population-based model, as illustrated in FIG. 5. In the example shown in FIG. 5, processing circuitry 110 retrieves, e.g., from memory 120 or from a remote database, population-based data including one or more first blood pressure values measured at acquisition site 103 for a population of patients and one or more second blood pressure values that was measured at reference site 105 for a population of patients (measured contemporaneous with the first blood pressure) (502).

The technique illustrated in FIG. 5 also includes determining, by processing circuitry 110, an association (e.g., relationship) between the first blood pressure and the second blood pressure (504). For example, determining the association may include parameterizing two or more sets of first blood pressures and second blood pressure measured contemporaneously. In some examples, the technique may include storing in memory 120 a look-up table, equation, or other physiological model based on the determined association. In some examples, rather than determining the association, processing circuitry 110 may retrieve, e.g., from memory 120 or from a remote database, the association (e.g., relationship) between the first blood pressure and the second blood pressure, such as a stored look-up table, equation, or other population-based model. In some examples, the technique may include automatically filtering, by processing circuitry 110, the population-based data based on demographic data associated with each set of first blood pressures and second blood pressures. Processing circuitry 110 determines the altered blood pressure value based on the population model base association (506). In this way, the technique illustrated in FIG. 5 includes determining, by processing circuitry 110, a relationship between the acquisition blood pressure and the reference blood pressure using a population-based model based on a predetermined association between a first set blood pressures at acquisition site 103 and a second set blood pressures at reference site 105.

Figure 6:
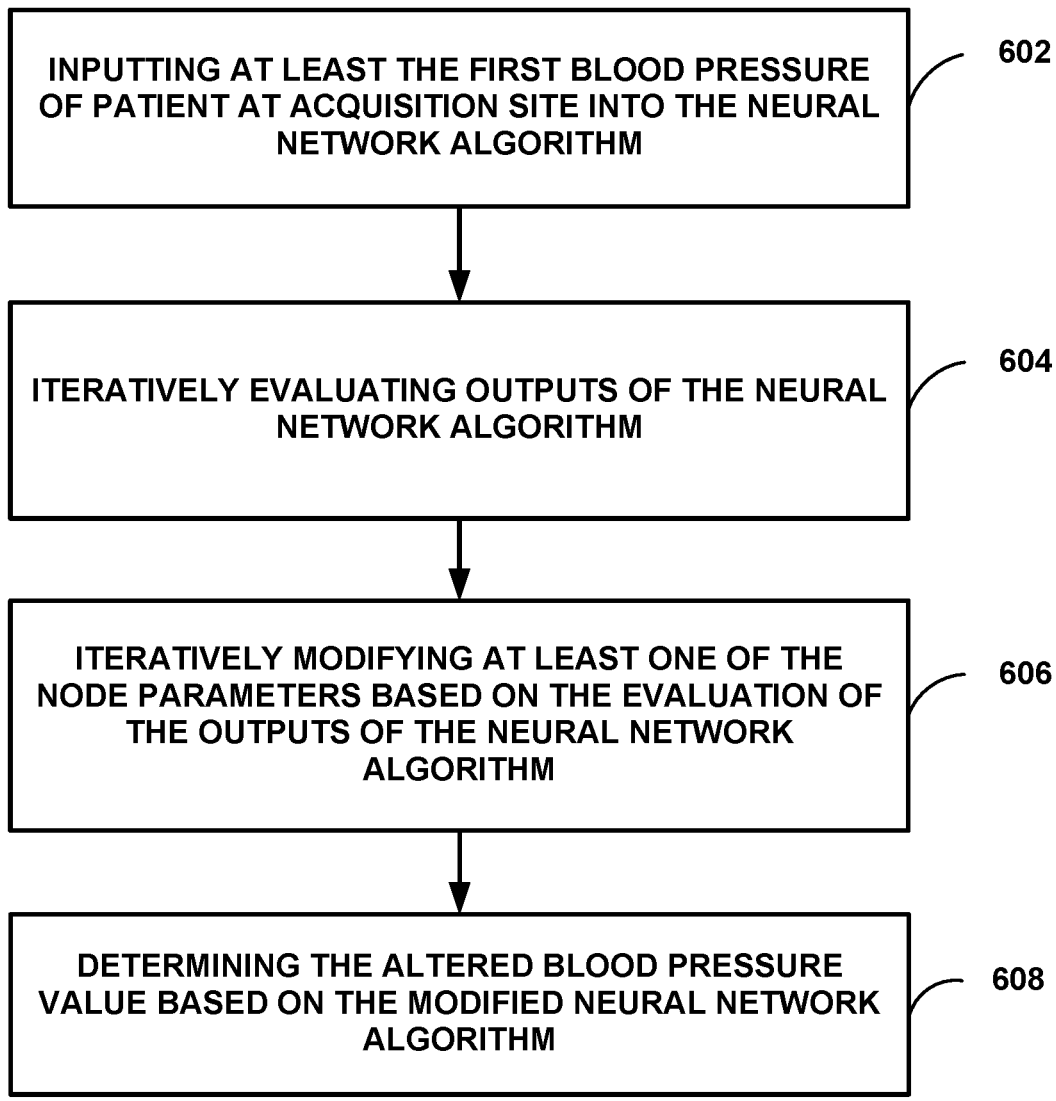

In some examples, determining the altered blood pressure value (304) may include using a neural network algorithm, as illustrated in FIG. 6. The technique illustrated in FIG. 6 includes, inputting, by processing circuitry 110, at least the first blood pressure of patient 101 at acquisition site 103 into the neural network algorithm (602), as described above. In some examples, processing circuitry 110 may input inputting training data, such as patient specific data or population-based data, into the neural network algorithm to tune the node parameters. The technique illustrated in FIG. 6 includes, iteratively evaluating, by processing circuitry 110, outputs of the neural network algorithm (604). The outputs may include the second blood pressure of patient 101 at reference site 105. The technique illustrated in FIG. 6 includes, iteratively modifying, by processing circuitry 110, at least one of the node parameters based on the evaluation of the outputs of the neural network algorithm (606). Processing circuitry 100 may determine the altered blood pressure value based on the modified neural network algorithm (608). In this way, the technique illustrated in FIG. 6 includes determining, by processing circuitry 110, a relationship between the acquisition blood pressure and the reference blood pressure using a neural network algorithm including a plurality of nodes, at least some of the nodes having node parameters.

Figure 7:
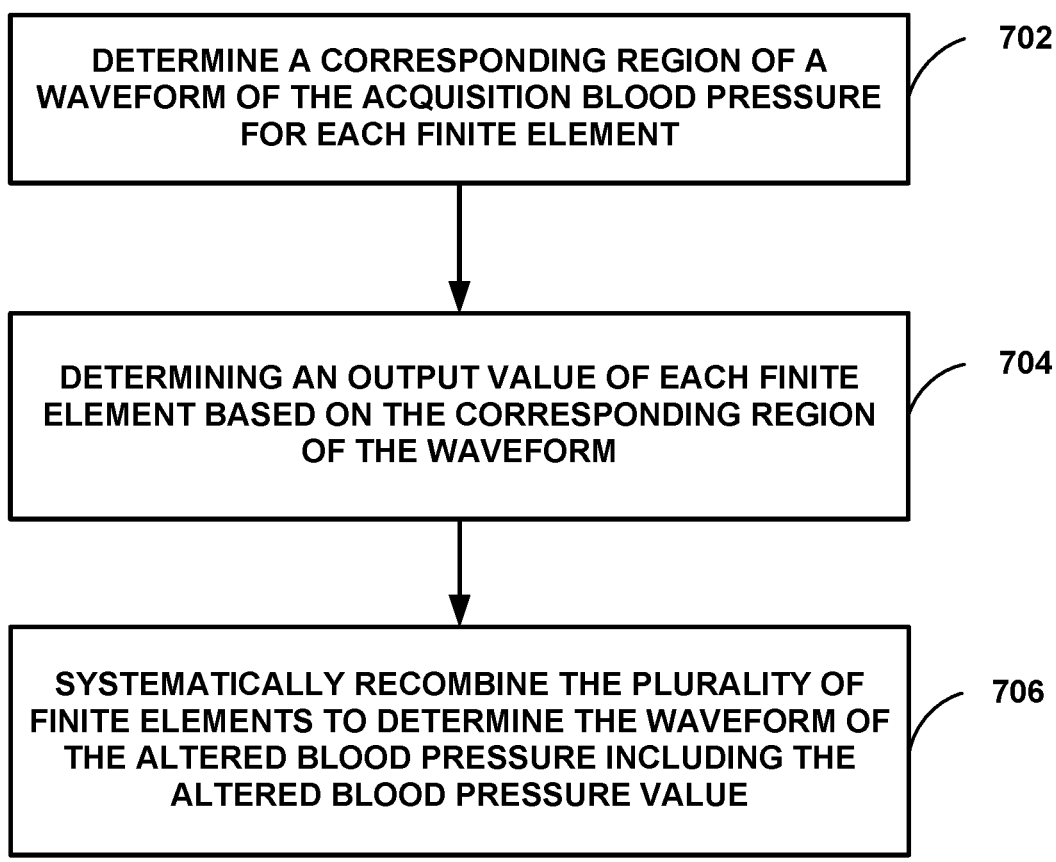

As illustrated in FIG. 7, in some examples, processing circuitry 110 may determine the altered blood pressure (304) may include using finite element analysis. In some examples, processing circuitry 110 determines a plurality of finite elements. Each finite element the plurality of finite elements may include one or more equations defined by the parameterized relation of training data, such as patient specific data or population-based data, as discussed above. The technique illustrated in FIG. 7 includes determining, by processing circuitry 110, a corresponding region of a waveform of the acquisition blood pressure for each finite element of the plurality of finite elements (702). Processing circuitry 110 may determine an output value of each finite element of the plurality of finite elements based on the corresponding region of the waveform (704). In some examples, processing circuitry 110 systematically recombines the plurality of finite elements to determine the waveform of the altered blood pressure including the altered blood pressure value (706). In this way, the technique illustrated in FIG. 7 includes determining, by processing circuitry 110, a relationship between the acquisition blood pressure and the reference blood pressure using a finite element model based on a plurality of finite elements configured to model an association between the first blood pressure of patient 101 at acquisition site 103 and the second blood pressure of patient 101 at reference site 105.

The techniques described in this disclosure, including those attributed to device 100, processing circuitry 110, control circuitry 122, sensing circuitries 140, 142, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully impplemented in one or more circuits or logic elements.

Clause 1. A method comprising: receiving, by processing circuitry, a blood pressure signal indicative of an acquisition blood pressure of a patient at an acquisition site and an oxygen saturation signal indicative of an oxygen saturation of the patient; determining, by the processing circuitry, an altered blood pressure value indicative of a reference blood pressure of the patient at a reference site based on the blood pressure signal; determining, by the processing circuitry, a value indicative of the autoregulation status of the patient based on the altered blood pressure value and the oxygen saturation signal; and providing, by the processing circuitry, a signal indicative of the autoregulation status of the patient to an output device.

Clause 2. The method of clause 1, wherein determining the altered blood pressure value comprises determining the altered blood pressure value based on mapping the acquisition blood pressure to the reference blood pressure.

Clause 3. The method of clause 2, wherein the mapping uses at least one of a physiological model, a population-based model, a neural network algorithm, or a finite element model to associate a first blood pressure of the patient at the acquisition site with a second blood pressure of the patient at the reference site.

Clause 4. The method of any one of clauses 1 through 3, wherein determining the altered blood pressure comprises determining a relationship between the acquisition blood pressure and the reference blood pressure using a physiological model based on a predetermined association between a first blood pressure of the patient at the acquisition site and a second blood pressure of the patient at the reference site.

Clause 5. The method of any one of clauses 1 through 4, wherein determining the altered blood pressure comprises determining a relationship between the acquisition blood pressure and the reference blood pressure using a population-based model based on a predetermined association between a first set blood pressures at the acquisition site and a second set blood pressures at the reference site.

Clause 6. The method of any one of clauses 1 through 5, wherein determining the altered blood pressure value comprises determining a relationship between the acquisition blood pressure and the reference blood pressure using a neural network algorithm comprising a plurality of nodes, at least some of the nodes having node parameters, by: inputting at least the first blood pressure of the patient at the acquisition site into the neural network algorithm; iteratively evaluating outputs of the neural network algorithm, wherein the outputs comprise the second blood pressure of the patient at the reference site; iteratively modifying at least one of the node parameters based on the evaluation of the outputs of the neural network algorithm; and determining the altered blood pressure value based on the modified neural network algorithm.

Clause 7. The method of any one of clauses 1 through 6, wherein determining the altered blood pressure comprises determining a relationship between the acquisition blood pressure and the reference blood pressure using a finite element model based on a plurality of finite elements configured to model an association between the first blood pressure of the patient at the acquisition site and the second blood pressure of the patient at the reference site.

Clause 8. The method of any one of clause 2 through 7, wherein the mapping accounts for differences in hydrostatic pressure between the acquisition blood pressure of the patient at the acquisition site and the reference blood pressure of the patient at the reference site.

Clause 9. The method of any one of clauses 2 through 8, wherein the mapping accounts for morphological differences in the waveforms of the acquisition blood pressure of the patient at the acquisition site and the reference blood pressure of the patient at the reference site.

Clause 10. The method of any one of clauses 1 through 9, wherein the blood pressure signal comprises a plurality of blood pressure signals, each indicative of a blood pressure of the patient at a respective acquisition site, wherein determining the altered blood pressure value indicative of a reference blood pressure of the patient at a reference site is based on the plurality of blood pressure signals.

Clause 11. The method of any one of clauses 1 through 10, wherein determining the value indicative of the autoregulation status of the patient comprises determining at least one of a lower limit of autoregulation or an upper limit of autoregulation based on the altered blood pressure value.

Clause 12. The method of any one of clauses 1 through 11, wherein receiving the blood pressure signal comprises noninvasively measuring the blood pressure of the patient at the acquisition site.

Clause 13. The method of any one of clauses 1 through 11, wherein the acquisition site comprises at least one of a femoral artery, a radial artery, a dorsalis pedis artery, or a brachial artery of the patient.

Clause 14. The method of any one of clauses 1 through 12, wherein the reference site comprises at least one of a femoral artery or a middle cerebral artery.

Clause 15. A system comprising: a blood pressure sensor configured to generate a blood pressure signal indicative of an acquisition blood pressure of a patient at an acquisition site; an oxygen saturation sensor configured to generate an oxygen saturation signal indicative of an oxygen saturation of the patient; and processing circuitry configured to: receive the blood pressure signal from the blood pressure sensor; receive the oxygen saturation signal from the oxygen saturation sensor; determine an altered blood pressure value indicative of a reference blood pressure of the patient at a reference site based on the blood pressure signal; determine a value indicative of the autoregulation status of the patient based on the altered blood pressure value and the oxygen saturation signal; and provide a signal indicative of the autoregulation status of the patient to an output device.

Clause 16. The system of clause 15, wherein the processing circuitry is configured to determine the altered blood pressure by at least determining the altered blood pressure value based on mapping the acquisition blood pressure to the reference blood pressure.

Clause 17. The system of clause 16, wherein processing circuitry is configured to map the acquisition blood pressure to the reference blood pressure using at least one of a physiological model, a neural network algorithm, a population-based model, or a finite element model to associate a first blood pressure of the patient at the acquisition site and a second blood pressure of the patient at the reference site.

Clause 18. The system of any one of clauses 15 through 17, wherein the processing circuitry is configured to determine the altered blood pressure by at least determining a relationship between the acquisition blood pressure and the reference blood pressure using a physiological model based on a predetermined association between a first blood pressure of the patient at the acquisition site and a second blood pressure of the patient at the reference site.

Clause 19. The system of any one of clauses 15 through 18, wherein the processing circuitry is configured to determine the altered blood pressure by at least determining a relationship between the acquisition blood pressure and the reference blood pressure using a neural network algorithm comprising a plurality of nodes, at least some of the nodes having node parameters, wherein the processing circuitry is configured to determine the relationship between the acquisition blood pressure and the reference blood pressure using the neural network algorithm by at least: inputting at least the first blood pressure of the patient at the acquisition site to the neural network algorithm; iteratively evaluating outputs of the neural network algorithm, wherein the outputs comprise the second blood pressure of the patient at the reference site; iteratively modifying at least one of the node parameters based on the evaluation of the outputs of the neural network algorithm; and determining the altered blood pressure value based on the modified neural network algorithm.

Clause 20. The system of any one of clauses 15 through 19, wherein the processing circuitry is configured to determine the altered blood pressure by at least determining a relationship between the acquisition blood pressure and the reference blood pressure using a population-based model based on a predetermined association between a first set blood pressures at the acquisition site and a second set blood pressures at the reference site.

Clause 21. The system of any one of clauses 15 through 20, wherein the processing circuitry is configured to determine the altered blood pressure by at least determining a relationship between the acquisition blood pressure and the reference blood pressure using a finite element model based on a plurality of finite elements configured to model an association between the first blood pressure of the patient at the acquisition site and the second blood pressure of the patient at the reference site.

Clause 22. The system of any one of clauses 16 through 21, wherein the mapping accounts for differences in hydrostatic pressure between the acquisition blood pressure of the patient at the acquisition site and the reference blood pressure of the patient at the reference site.

Clause 23. The system of any one of clauses 16 through 22, wherein the mapping accounts for morphological differences in the waveforms of the acquisition blood pressure of the patient at the acquisition site and the reference blood pressure of the patient at the reference site.

Clause 24. The system of any one of clauses 15 through 23, wherein the blood pressure signal comprises a plurality of blood pressure signals, each indicative of a blood pressure of the patient at a respective acquisition site, wherein the processing circuitry is configured to determine the altered blood pressure value based on the plurality of blood pressure signals.

Clause 25. The system of any one of clauses 15 through 24, wherein the processing circuitry is configured to determine the value indicative of the autoregulation status of the patient by at least determining at least one of a lower limit of autoregulation or an upper limit of autoregulation based on the altered blood pressure value.

Clause 26. The system of any one of clauses 15 through 25, wherein the blood pressure sensor is configured to non-invasively measure the blood pressure of the patient at the acquisition site to generate the blood pressure signal.

Clause 27. The system of any one of clauses 15 through 26, wherein the acquisition site comprises at least one of a femoral artery, a radial artery, a dorsalis pedis artery, or a brachial artery of the patient.

Clause 28. The system of any one of clauses 15 through 27, wherein the reference site comprises at least one of a femoral artery or a middle cerebral artery.

Clause 29. A non-transitory computer readable storable medium comprising instructions that, when executed, cause processing circuitry to: receive a blood pressure signal indicative of a blood pressure of a patient at an acquisition site and an oxygen saturation signal indicative of an oxygen saturation of the patient; determine an altered blood pressure value indicative of a reference blood pressure of the patient at a reference site based on the blood pressure signal; determine a value indicative of the autoregulation status of the patient based on the altered blood pressure value and the oxygen saturation signal; and provide a signal indicative of the autoregulation status of the patient to an output device.

Clause 30. The non-transitory computer readable storable medium of clause 29, further comprising instructions that, when executed, cause the processing circuitry to perform the method of any one of clauses 2 through 14.

Various examples of the disclosure have been described. Any combination of the described systems, operations, or functions is contemplated. These and other examples are within the scope of the following claims.

What is claimed is:

1. A method comprising:
    receiving, by processing circuitry, a continuous blood pressure signal for a period of time indicative of an acquisition blood pressure of a patient at an acquisition site and an oxygen saturation signal indicative of an oxygen saturation of the patient, without receiving an additional blood pressure signal for the period of time indicative of a reference blood pressure of the patient at a reference site;
    determining, by the processing circuitry, a plurality of altered blood pressure values for the period of time based on mapping the continuous blood pressure signal to a stored association between the acquisition blood pressure and the reference blood pressure of the patient corresponding to the reference site, wherein the reference site is a femoral artery or in a brain of the patient;
    determining, by the processing circuitry, a value indicative of an autoregulation status of the patient based on the plurality of altered blood pressure values and the oxygen saturation signal; and
    providing, by the processing circuitry, a signal indicative of the autoregulation status of the patient to an output device.

2. The method of claim 1, wherein the stored association comprises a physiological model, a population-based model, a neural network algorithm, or a finite element model to associate a first blood pressure of the patient at the acquisition site with a second blood pressure of the patient at the reference site.

3. The method of claim 2, wherein the first blood pressure and the second blood pressure are stored prior to the period of time.

4. The method of claim 1, wherein the stored association comprises a physiological model comprising respective a predetermined associations between respective stored acquisition blood pressures of the patient at the acquisition site and respective stored reference blood pressures of the patient at the reference site.

5. The method of claim 1, wherein the stored association comprises a population-based model comprising respective predetermined associations between respective stored acquisition blood pressures and respective stored reference blood pressures, wherein the predetermined association is not patient specific.

6. The method of claim 1, wherein the stored association comprises a neural network algorithm comprising a plurality of nodes, at least some of the nodes of the plurality of nodes comprise node parameters, and determining the plurality of altered blood pressure values comprises:
inputting at least a first blood pressure of the patient at the acquisition site into the neural network algorithm;
iteratively evaluating outputs of the neural network algorithm, wherein the outputs comprise a second blood pressure of the patient at the reference site;
iteratively modifying at least one of the node parameters based on the evaluation of the outputs of the neural network algorithm; and
determining the plurality of altered blood pressure values based on the modified neural network algorithm.

7. The method of claim 1, wherein the stored association comprises a finite element model based on a plurality of finite elements configured to model an association between a first blood pressure of the patient at the acquisition site and a second blood pressure of the patient at the reference site.

8. The method of claim 1, wherein the mapping accounts for differences in hydrostatic pressure between the acquisition blood pressure of the patient at the acquisition site and the reference blood pressure of the patient at the reference site.

9. The method of claim 1, wherein the mapping accounts for morphological differences in a respective shape of a respective waveform of the acquisition blood pressure of the patient at the acquisition site and a respective shape of a respective waveform of the reference blood pressure of the patient at the reference site.

10. The method of claim 1, wherein the continuous blood pressure signal comprises a plurality of continuous blood pressure signals, each indicative of a blood pressure of the patient at a respective acquisition site, wherein determining the plurality of altered blood pressure values is based on the plurality of continuous blood pressure signals.

11. The method of claim 1, wherein determining the value indicative of the autoregulation status of the patient comprises determining at least one of a lower limit of autoregulation or an upper limit of autoregulation.

12. The method of claim 1, wherein receiving the continuous blood pressure signal comprises non-invasively measuring the acquisition blood pressure of the patient at the acquisition site.

13. The method of claim 1, wherein the acquisition site comprises at least one of the femoral artery, a radial artery, a dorsalis pedis artery, or a brachial artery of the patient, and wherein the reference site is in the brain of the patient.

14. The method of claim 1, wherein the reference site comprises at least one of the femoral artery or a middle cerebral artery.

15. A system comprising:
a blood pressure sensor configured to generate a continuous blood pressure signal indicative of an acquisition blood pressure of a patient at an acquisition site;
an oxygen saturation sensor configured to generate an oxygen saturation signal indicative of an oxygen saturation of the patient; and
processing circuitry configured to:
receive the continuous blood pressure signal for a period of time from the blood pressure sensor, without receiving an additional blood pressure signal for the period of time indicative of a reference blood pressure of the patient at a reference site;
receive the oxygen saturation signal from the oxygen saturation sensor;
determine a plurality of altered blood pressure values for the period of time based on mapping the continuous blood pressure signal to a stored association between the acquisition blood pressure and the reference blood pressure of the patient corresponding to the reference site, wherein the reference site is a femoral artery or in a brain of the patient;
determine a value indicative of an autoregulation status of the patient based on the plurality of altered blood pressure values and the oxygen saturation signal; and
provide a signal indicative of the autoregulation status of the patient to an output device.

16. The system of claim 15, wherein the stored association comprises a physiological model, a neural network algorithm, a population-based model, or a finite element model to associate a first blood pressure of the patient at the acquisition site and a second blood pressure of the patient at the reference site.

17. The system of claim 15, wherein the stored association comprises a physiological model comprising respective predetermined associations between respective stored acquisition blood pressures of the patient at the acquisition site and respective stored reference blood pressures of the patient at the reference site.

18. The system of claim 17, wherein the physiological model comprises a look-up table comprising the respective stored acquisition blood pressures and the respective stored reference blood pressures, wherein the respective stored acquisition blood pressures comprise a plurality of first blood pressures of the patient at the acquisition site and the respective stored reference blood pressures comprises a plurality of second blood pressures of the patient at the reference site.

19. The system of claim 18, wherein the processing circuitry is configured to:
determine the respective predetermined associations of the physiological model based on parameterizing the plurality of first blood pressures and the plurality of second blood pressures.

20. The system of claim 15, wherein the stored association comprises a neural network algorithm comprising a plurality of nodes, at least some of the nodes of the plurality of nodes comprise node parameters, wherein the processing circuitry is configured to determine the plurality of altered blood pressure values using the neural network algorithm by at least:
inputting at least a first blood pressure of the patient at the acquisition site to the neural network algorithm;
iteratively evaluating outputs of the neural network algorithm, wherein the outputs comprise a second blood pressure of the patient at the reference site;
iteratively modifying at least one of the node parameters based on the evaluation of the outputs of the neural network algorithm; and
determining the plurality of altered blood pressure values based on the modified neural network algorithm.

21. The system of claim 15, wherein the stored association comprises a population-based model comprising respective predetermined associations between respective stored acquisition blood pressures and respective stored reference blood pressures, wherein the predetermined association is not patient specific.

22. The system of claim 21, wherein the processing circuitry is configured to:
   receive a demographic indicator of the patient;
   select a sub-set of the population-based model associated with the demographic indicator of the patient; and
   determine the plurality of altered blood pressure values by at least determining a relationship between the acquisition blood pressure and blood pressure of the patient at the reference site using the sub-set of the population-based model.

23. The system of claim 15, wherein the stored association comprises a finite element model based on a plurality of finite elements configured to model an association between a first blood pressure of the patient at the acquisition site and a second blood pressure of the patient at the reference site.

24. The system of claim 15, wherein the mapping accounts for differences in hydrostatic pressure between the acquisition blood pressure of the patient at the acquisition site and the reference blood pressure of the patient at the reference site.

25. The system of claim 15, wherein the mapping accounts for morphological differences in a respective shape of a respective waveform of the acquisition blood pressure of the patient at the acquisition site and a respective shape of a respective waveform of the blood pressure of the patient at the reference site.

26. The system of claim 25, wherein the morphological differences include a shape of a waveform of the acquisition blood pressure, a systolic upstroke of the waveform, a systolic peak pressure of the waveform, a systolic decline of the waveform, a dicrotic notch of the waveform, a diastolic runoff of the waveform, or an end-diastolic pressure of the waveform.

27. The system of claim 15, wherein the continuous blood pressure signal comprises a plurality of continuous blood pressure signals, each indicative of a blood pressure of the patient at a respective acquisition site, wherein the processing circuitry is configured to determine the plurality of altered blood pressure values based on the plurality of continuous blood pressure signals.

28. The system of claim 15, wherein the processing circuitry is configured to determine the value indicative of the autoregulation status of the patient by at least determining at least one of a lower limit of autoregulation or an upper limit of autoregulation.

29. The system of claim 15, wherein the blood pressure sensor is configured to non-invasively measure the acquisition blood pressure of the patient at the acquisition site to generate the continuous blood pressure signal.

30. The system of claim 15, wherein the acquisition site comprises at least one of the femoral artery, a radial artery, a dorsalis pedis artery, or a brachial artery of the patient, and wherein the reference site is in the brain of the patient.

31. The system of claim 15, wherein the reference site comprises at least one of the femoral artery or a middle cerebral artery.

32. The system of claim 15, wherein the acquisition site is at a peripheral site of the patient, and the reference site is in the brain of the patient.

33. The system of claim 15, wherein the processing circuitry is configured to determine the plurality of altered blood pressure values by at least transforming a timing of one or more positions of a waveform of the acquisition blood pressure to a corresponding one or more positions of a waveform of the blood pressure at the reference site.

34. The system of claim 15, wherein the stored association comprises a look-up table comprising the reference blood pressure of the patient corresponding to the reference site, and the processing circuitry is configured to determine the reference blood pressure of the patient based on the acquisition blood pressure and the look-up table.

35. A non-transitory computer readable storable medium comprising instructions that, when executed, cause processing circuitry to:
   receive a continuous blood pressure signal for a period of time indicative of a blood pressure of a patient at an acquisition site and an oxygen saturation signal indicative of an oxygen saturation of the patient, without receiving an additional blood pressure signal for the period of time indicative of a blood pressure of the patient at a reference site;
   determine a plurality of altered blood pressure values for the period of time based on mapping the continuous blood pressure signal to a stored association between the blood pressure at the acquisition site and the blood pressure at the reference site, wherein the reference site is a femoral artery or in a brain of the patient;
   determine a value indicative of an autoregulation status of the patient based on the plurality of altered blood pressure values and the oxygen saturation signal; and
   provide a signal indicative of the autoregulation status of the patient to an output device.

* * * * *